United States Patent [19]

Sasmor et al.

[11] Patent Number: 4,825,869
[45] Date of Patent: May 2, 1989

[54] SYSTEM FOR AUTOMATICALLY PERFORMING A CLINICAL ASSESSMENT OF AN IMPLANTED PACER BASED ON INFORMATION THAT IS TELEMETRICALLY RECEIVED

[75] Inventors: Louis Sasmor; Edward D. Smith, both of Miami, Fla.

[73] Assignee: Telectronics N.V., Netherlands Antilles

[21] Appl. No.: 101,757

[22] Filed: Sep. 28, 1987

[51] Int. Cl.[4] ............................ A61N 1/00; H05G 2/00
[52] U.S. Cl. ................................................ 128/419 PT
[58] Field of Search .................. 128/419 PT, 419 PG, 128/630, 631, 697, 903

[56] References Cited

U.S. PATENT DOCUMENTS

| | | | |
|---|---|---|---|
| 4,223,678 | 9/1980 | Langer et al. | 128/903 |
| 4,550,370 | 10/1985 | Baker | 128/419 PG |
| 4,596,255 | 6/1986 | Snell et al. | 128/419 PT |
| 4,705,042 | 11/1987 | Giurtino | 128/419 PT |

OTHER PUBLICATIONS

Dassen, et al., "Evaluation of Pacemaker Performance Using Computer Simulation" *PACE*, vol. 8, pp. 795-805 (Nov.-Dec. 1985).

Olson, et al., "Pacemaker Diagnostic Diagrams" *PACE*, vol. 8, pp. 691-700 (Sep.-Oct. 1985).

Sutton, et al., "Interpretation of Dual Chamber Pacemaker Electrocardiograms", *PACE*, vol. 8, pp. 6-16 (Jan.-Feb. 1985).

Bernstein, et al., "Notation System and Overlay Diagrams for the Analysis of Paced Electrocardiograms", *PACE*, vol. 6, pp. 73-80 (Jan.-Feb. 1983).

Yeh, "Electrogram Evaluation By The Pacemaker Follow-Up Station", *Cleveland Clinic Foundation* (May 9, 1985).

Manoli, et al., "An Algorithm for Arrhythmia Detection from Epicardial ECG", 37th *ACEMB*, p. 82 (Sep. 17-19, 1984).

*Primary Examiner*—Francis Jaworski
*Assistant Examiner*—George Manuel
*Attorney, Agent, or Firm*—Gerstman & Ellis, Ltd.

[57] ABSTRACT

A cardiac pacer analysis system which is external to the patient is provided for an implanted pacer having patient history stored within the pacer. Information is transmitted from the pacer, and is received, stored and processed. Events in the received information are identified and characterized, observed problems are identified, probable causes of observed problems are indicated and possible corrective actions are provided. The results of the analyses are displayed for the clinician.

16 Claims, 16 Drawing Sheets

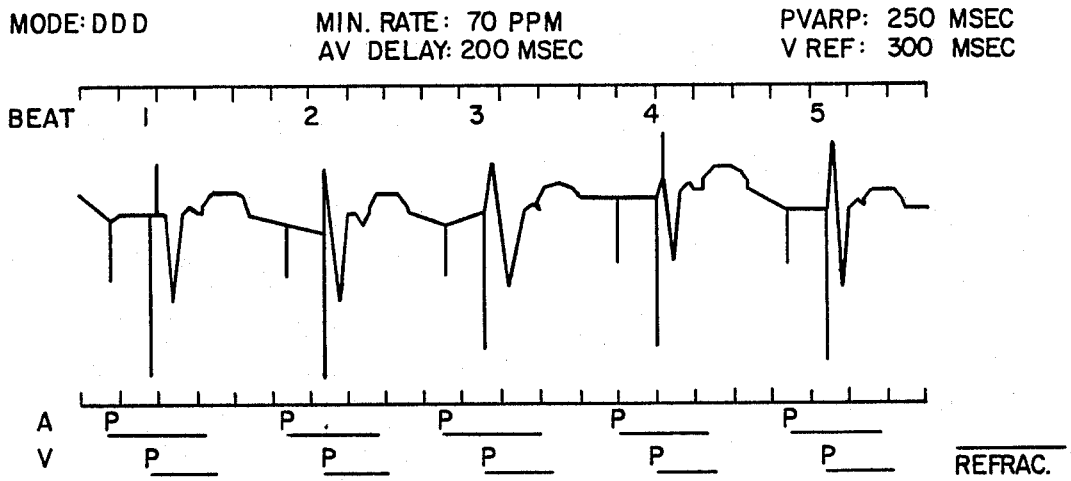

| MODE: DDD | MIN. RATE: 70 PPM | PVARP: 250 MSEC |
|---|---|---|
| | AV DELAY: 200 MSEC | V REF: 300 MSEC |

VENTRICULAR CHANNEL:

SENSING WAS NOT OBSERVED
    PACING TIMING IS NOT NORMAL
    CAPTURE IS NORMAL
    REFRACTORY TIMING IS NORMAL

ATRIAL CHANNEL:

SENSING WAS NOT OBSERVED
    PACING TIMING IS NORMAL
    REFRACTORY TIMING IS NORMAL

••••• COMPLETE LOSS OF ATRIAL CAPTURE •••••
        OBSERVED ON BEATS 1,2,3,4,5
        ATRIAL OUTPUT VALUES ARE 4.0ma AND 0.4msec
          (HIGHER VALUES ARE AVAILABLE)
        PATIENT'S PRE-PACING ECG SHOWED: CHB, WIDE QRS
        PATIENT'S PRE IMPLANT SYMPTOMS: SYNCOPE

••••• RETROGRADE P WAVES •••••
        OBSERVED ON BEATS 1,2,3,4,5
        IN ATRIAL REFRACTORY PERIOD AND WERE PROPERLY NOT SENSED
        POSSIBLY CAUSED BY THE LOSS OF ATRIAL CAPTURE

RECOMMENDATION:

PERFORM ATRIAL THRESHOLD TEST
    INCREASE ATRIAL OUTPUT TO RE-GAIN ATRIAL CAPTURE

FIG. 2

SURFACE ECG (FOR REFERENCE PURPOSES ONLY)

NORMAL, ACCEPTABLE ATRIAL ICEG SIGNAL

UNACCEPTABLE ATRIAL ICEG SIGNAL
SIGNAL LEVEL TOO LOW

UNACCEPTABLE ATRIAL ICEG SIGNAL
NOISE LEVEL TOO HIGH

UNACCEPTABLE ATRIAL ICEG SIGNAL
AMPLIFIER SATURATED AFTER PACING SPIKE

FIG. 5A
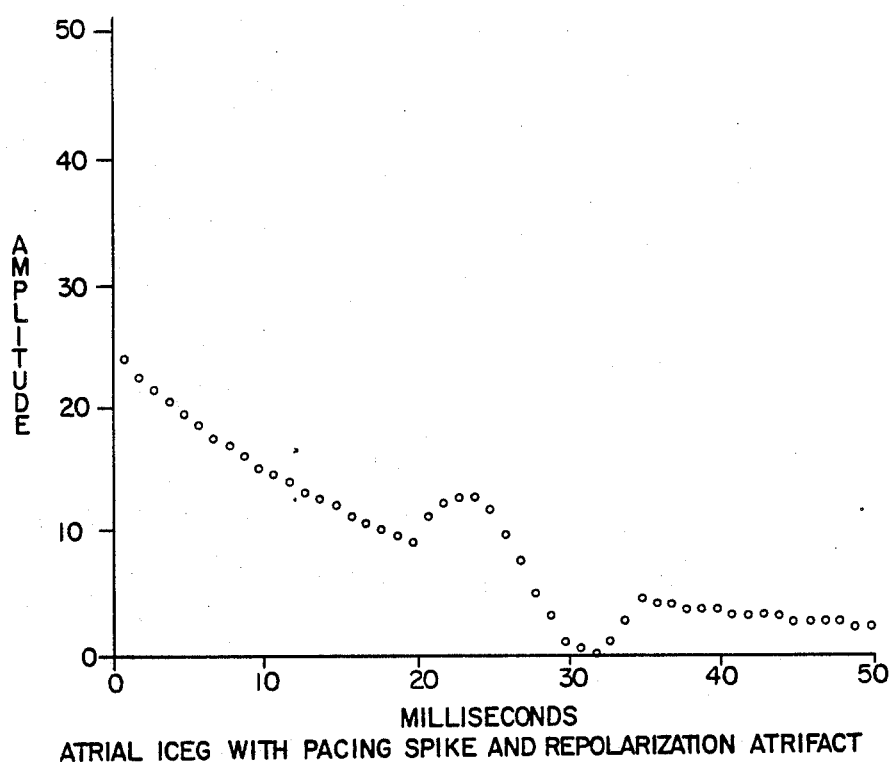
ATRIAL ICEG WITH PACING SPIKE AND REPOLARIZATION ATRIFACT
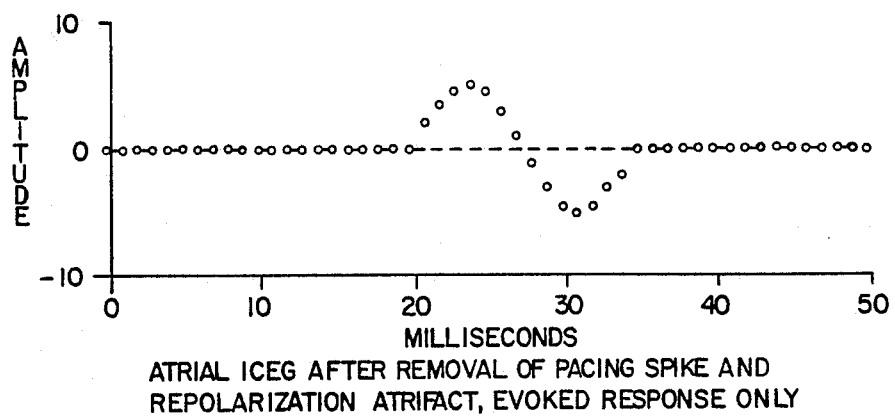
ATRIAL ICEG AFTER REMOVAL OF PACING SPIKE AND
REPOLARIZATION ATRIFACT, EVOKED RESPONSE ONLY
FIG. 5B

NOTE: ▭ INDICATES CANDIDATE AREAS IDENTIFIED BY THE SIMPLE DETECTOR

FIG. 7

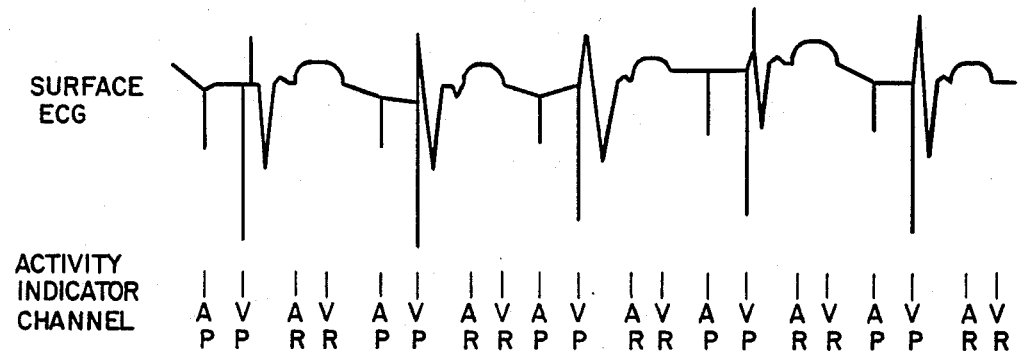

WHERE: AP IS ATRIAL PACE ACTIVITY INDICATOR
VP IS VENTRICULAR PACE ACTIVITY INDICATOR
AR IS END OF ATRIAL REFACTORY PERIOD ACTIVITY INDICATOR
VR IS END OF VENTRICULAR REFRACTORY PERIOD ACTIVITY INDICATOR

EVENT LIST

| EVENT # | TIME | CH | SPONT. ACTIVITY | INDICATORS SENSE | INDICATORS PACE | OUTPUT PULSE | EVOKED RESPONSE | TIME TO END REFRACTORY ATRIAL | TIME TO END REFRACTORY VENTRICULAR |
|---|---|---|---|---|---|---|---|---|---|
| 1 | 404 | A | ABSENT | NO | YES | PRESENT | ABSENT | 0 | 0 |
| 2 | 605 | V | ABSENT | NO | YES | PRESENT | PRESENT | 0 | 0 |
| 3 | 864 | A | PRESENT | NO | NO | ABSENT | ABSENT | 41 | 142 |
| 4 | 1260 | A | ABSENT | NO | YES | PRESENT | ABSENT | 0 | 0 |
| 5 | 1463 | V | ABSENT | NO | YES | PRESENT | PRESENT | 0 | 0 |
| 6 | 1715 | A | PRESENT | NO | NO | ABSENT | ABSENT | 47 | 148 |
| 7 | 2122 | A | ABSENT | NO | YES | PRESENT | ABSENT | 0 | 0 |
| 8 | 2325 | V | ABSENT | NO | YES | PRESENT | PRESENT | 0 | 0 |
| 9 | 2582 | A | PRESENT | NO | NO | ABSENT | ABSENT | 44 | 143 |
| 10 | 2974 | A | ABSENT | NO | YES | PRESENT | ABSENT | 0 | 0 |
| 11 | 3173 | V | ABSENT | NO | YES | PRESENT | PRESENT | 0 | 0 |
| 12 | 3424 | A | PRESENT | NO | NO | ABSENT | ABSENT | 48 | 150 |
| 13 | 3831 | A | ABSENT | NO | NO | ABSENT | ABSENT | 0 | 0 |
| 14 | 4036 | V | ABSENT | NO | YES | PRESENT | PRESENT | 0 | 0 |
| 15 | 4277 | A | PRESENT | NO | NO | ABSENT | ABSENT | 49 | 151 |

FIG. 8

SURFACE ECG (FOR REFERENCE PURPOSES ONLY)

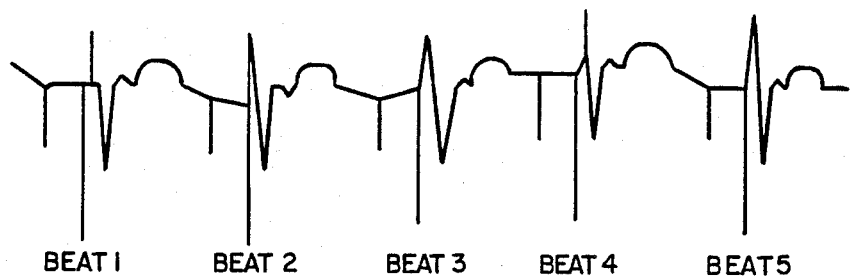

BEAT 1   BEAT 2   BEAT 3   BEAT 4   BEAT 5

FIG. 15B

EVENT STATUS SUMMARY RECORD

ATRIAL CHANNEL

| TYPE | STATUS | BEATS |
|---|---|---|
| SENSING | OK UNOBSERVED | 1 2 3 4 5 |
| SENSING | OK IGNORED | 1 2 3 4 5 |
| PACING | OK OUTPUT WHEN EXPECTED | 2 3 4 5 |
| PACING | OK OUTPUT TIMING UNCERTAIN | 1 |
| CAPTURE | NG NO CAPTURE | 1 2 3 4 5 |
| SPECIAL | IGNORED RETROGRADE P WAVE | 1 2 3 4 5 |

VENTRICULAR CHANNEL

| TYPE | STATUS | BEATS |
|---|---|---|
| SENSING | OK UNOBSERVED | 1 2 3 4 5 |
| PACING | OK OUTPUT WHEN EXPECTED | 1 2 3 4 5 |
| CAPTURE | OK CAPTURED | 1 2 3 4 5 |

FIG. 15A

SYSTEM FOR AUTOMATICALLY PERFORMING A CLINICAL ASSESSMENT OF AN IMPLANTED PACER BASED ON INFORMATION THAT IS TELEMETRICALLY RECEIVED

FIELD OF THE INVENTION

The present invention concerns a novel system for gathering and processing information for the purpose of determining whether or not an implanted cardiac pacer system is functioning properly.

BACKGROUND OF THE INVENTION

Modern implanted cardiac pacers have the ability to telemeter information to an external programming and/or receiving unit. In this manner, certain information concerning the pacer's characteristics, including mode, rate, battery level, etc. can be obtained. It is very desirable to be able to determine whether the implanted pacer is functioning properly; specifically, to determine whether the implanted pacer is supporting the patient as expected, given the pacer therapy described and programmed by the implanting or patient follow-up clinician. It would be extremely desirable to have the ability to analyze complex pacemaker modified electrocardiograms (ECGs), determine problems, relate the problems to the specific causes, and have the ability to recommend clinically acceptable actions.

SUMMARY OF THE INVENTION

In accordance with the present invention, a cardiac pacer analysis system is provided which non-invasively performs a detailed analysis of the functional status of the entire implanted pacemaker/patient system, rather than merely providing an annotated display of the ECG. The illustrative embodiment combines the surface ECG with telemetered atrial and ventricular ICEGs and activity indicators into a common structure for the simultaneous analyses of pacing antifacts to verify pacemaker output, of evoked potentials to verify capture, and of spontaneous cardiac activity to verify pacemaker sensing. It incorporates a detailed model of the specific pacemaker, and adjusts the actions of the model based on telemetered pacemaker programmed parameter values.

The illustrative embodiment analyzes the functions of and identifies problems with the entire pacemaker system, including the leads and the pacemaker's interactions with the patient. It combines the abnormal functionings observed on different beats into a structure of common underlying problem causes, using a knowledge base which includes both clinical and engineering expertise. It incorporates information stored in and telemetered from the pacemaker (such as lead location and implant date) as well as the telemetered results of automatically performed pacemaker measurements (such as battery voltage and lead impedance) in identifying problems.

The illustrative embodiment uses its clinically derived knowledge base plus patient and pacemaker information to recommend specific corrective actions that could be taken to rectify problems that have been identified.

The illustrative embodiment provides an English language annotated description of the analysis results, along with conventional graphics ECGs.

The illustrative embodiment receives data about the pacemaker and its interaction with the patient from both surface ECG signals and telemetric communications with the pacemaker. The telemetered data include programmed parameter vales, atrial and ventricular intra-cardiac electrograms, pacemaker activity indicators, the results of automatically performed pacemaker measurements, and patient history informaation previously stored in the pacemaker. These data are combined with a pre-stored knowledge base which encompasses the functional characteristics of the implanted pacemaker and the clinical interpretation of paced cardiac events.

The illustrative embodiment uses these data as information about the specific pacemaker/patient interactions, and via a combination of digital signal processing, emulation (modeling) of the pacemaker functions, and application of published and rules-of-thumb heuristic clinical interpretations of paced cardiac events, produces a comprehensive analysis of a patient's pacemaker modified ECG. It identifies normal and abnormal functional events, and summarizes these for the clinician; for any abnormal events, it identifies probable causes and lists appropriate possible diagnostic and therapeutic procedures.

A more detailed explanation of the invention is provided in the following descriptions and claims, and is illustrated in the accompanying drawings.

BRIEF DESCRIPTION OF THE DRAWINGS

FIG. 2 is a typical device hard copy output of the system of FIG. 1;

FIG. 5A illustrates an atrial ICEG with a pacing spike and repolarization atrifact;

FIG. 5B illustrates an atrial ICEG after removal of the spike and atrifact;

FIG. 7 illustrates the event list formatting;

FIG. 8 illustrates an example event list;

FIG. 15A illustrates an event status summary record that would be produced for the surface ECG illustrated in FIG. 15B;

FIG. 15B is an illustration of a sample (stylized) surface ECG;

DETAILED DESCRIPTION OF THE ILLUSTRATIVE EMBODIMENT

Figure 1:
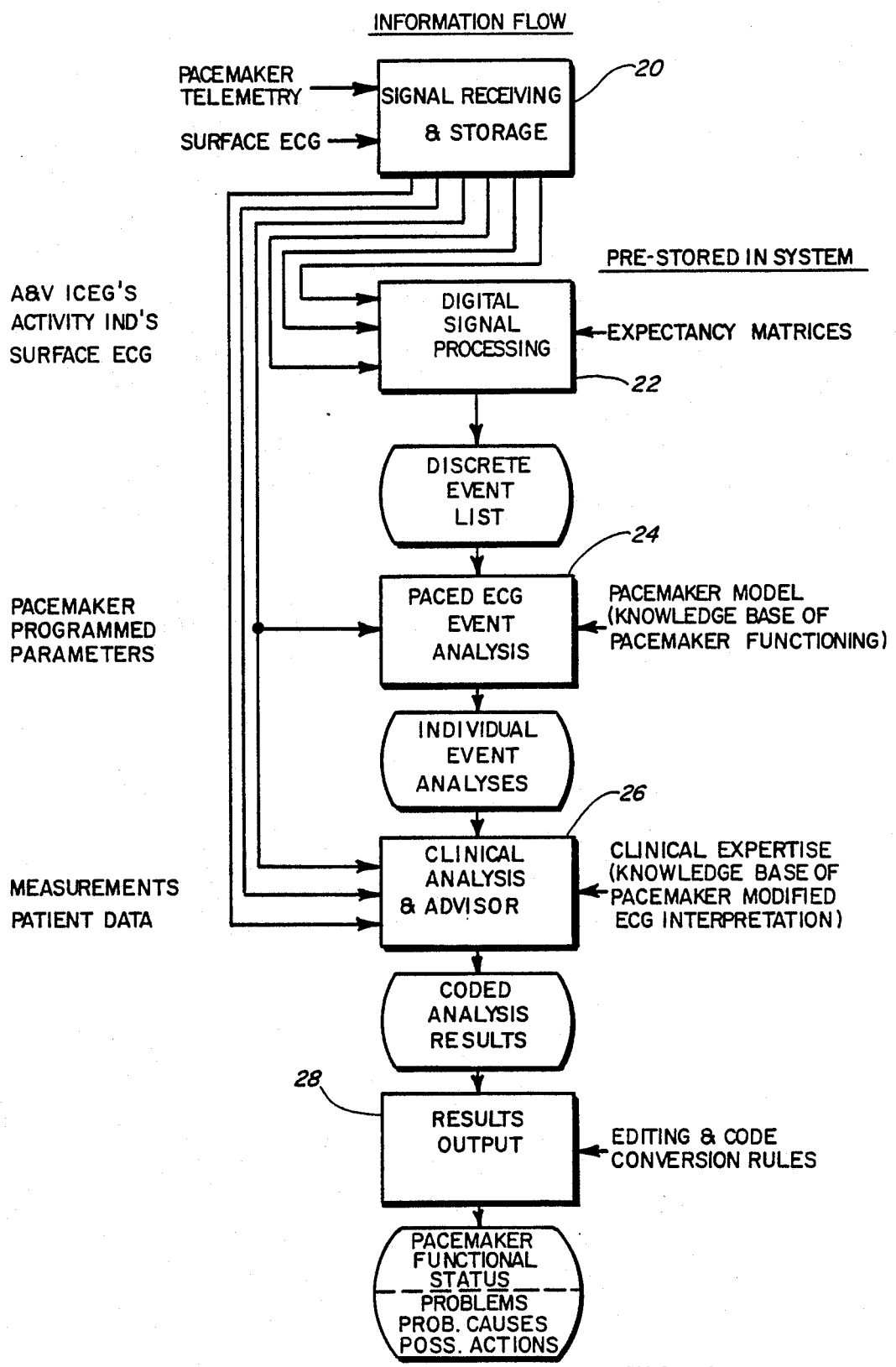
FIG. 1 is a block diagram of a cardiac pacer analysis system constructed in accordance with the principles of the present invention.

Referring to FIG. 1, the cardiac pacing analysis system of the present invention is embodied in a device including five major functional units:

The device consists of five major functional units:
1. A signal receiving and storage unit 20,
2. A digital signal processing unit 22,
3. A paced ECG event analysis unit 24,
4. A clinical analysis and advisor unit 26, and
5. A results output unit 28.

The signal receiving and storage unit 20 accepts surface ECG and telemetrically transmitted information from the pacemaker and stores it for later use by the remaining units. The next three units analyze the received information; the digital signal processing unit 22 identifies and characterizes the events in the received ECG data, the paced ECG event analysis unit 24 determines if the pacemaker functioned correctly at each event, and the clinical analysis and advisor unit 26 summarizes these results and identifies and observed problems and provides probable causes and possible corrective actions for them. The final unit, the results output unit 28, presents the results of the analyses to the clinician.

Figure 3:
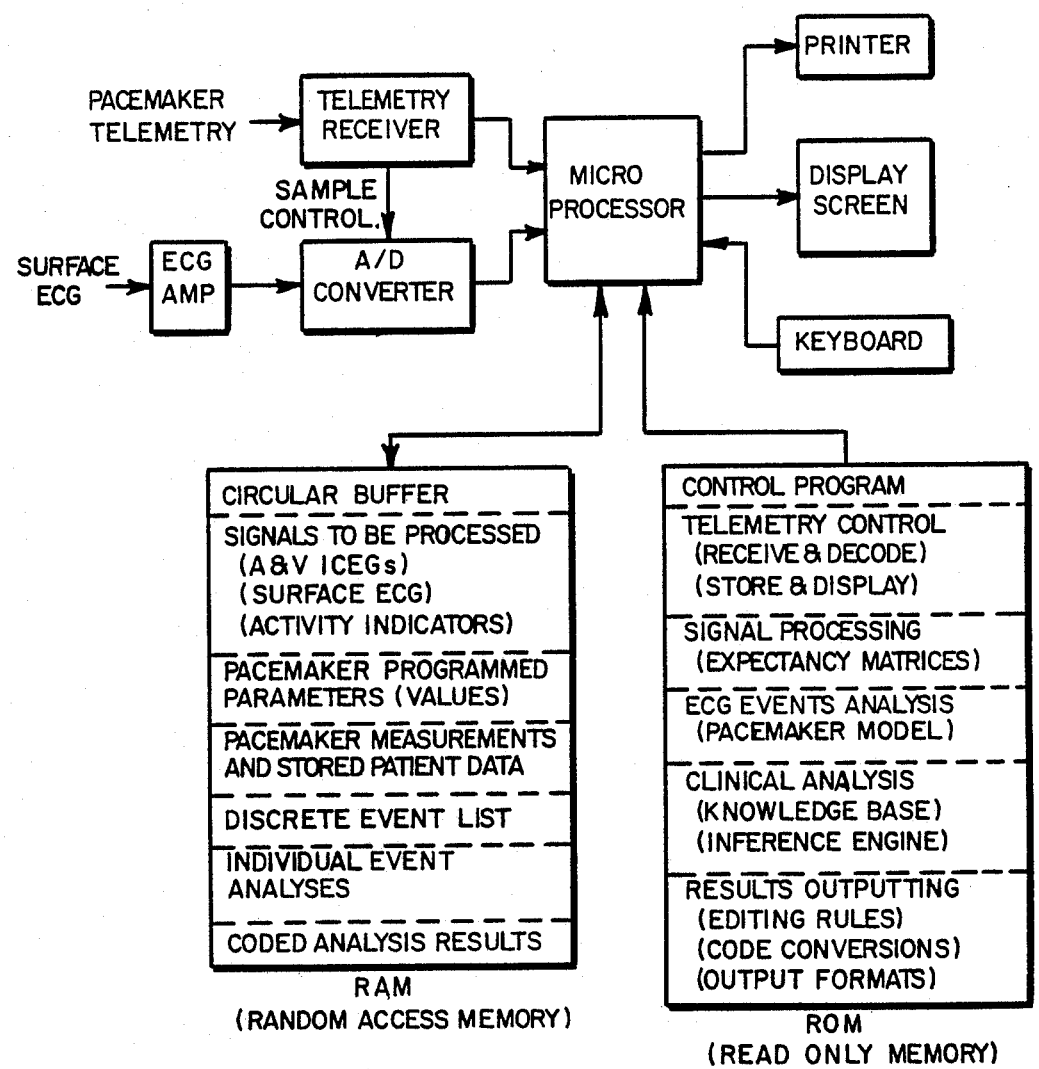
FIG. 3 illustrates the structure needed to implement the system of FIG. 1 in a microprocessor-based instrument.
Figure 4A:
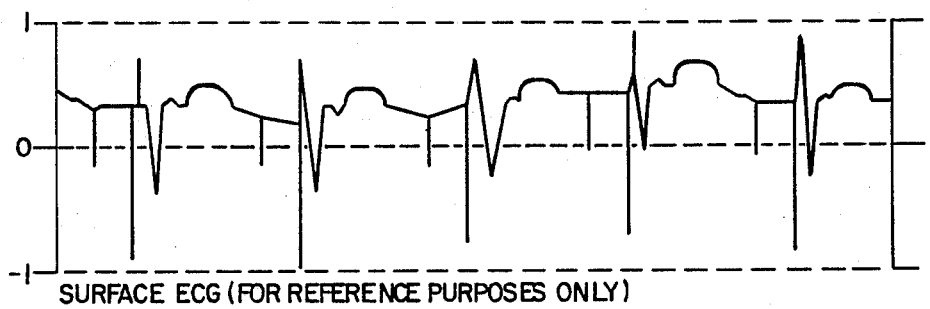
FIG. 4A illustrates a surface ECG.
Figure 4B:
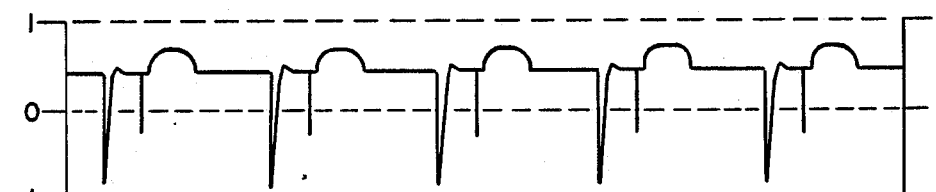
FIG. 4B illustrates a normal acceptable atrial ICEG signal.
Figure 4C:
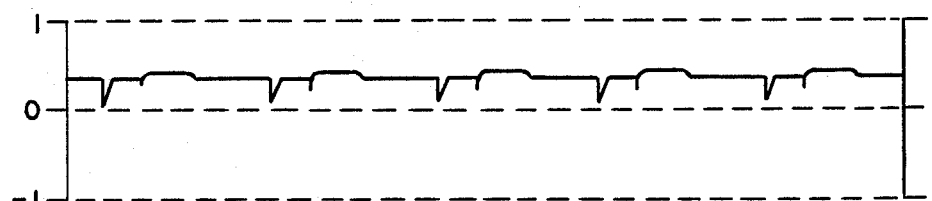
FIG. 4C illustrates an unacceptable atrial ICEG signal.
Figure 4D:
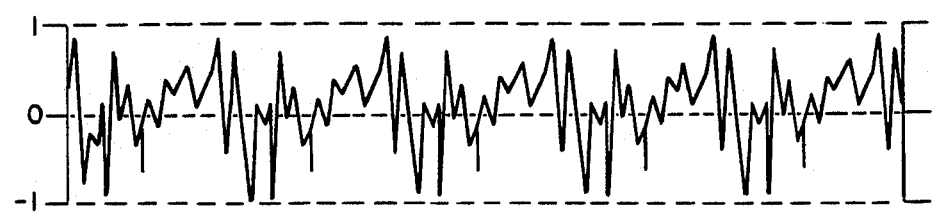
FIG. 4D illustrates an unacceptable atrial ICEG signal.
Figure 4E:
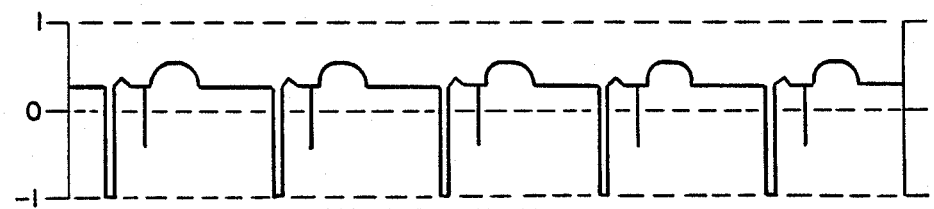
FIG. 4E illustrates an unacceptable atrial ICEG signal.

FIG. 1 shows how the information flows among the five units of the device, while FIG. 2 shows a typical device hard copy output. FIG. 3 shows the structure needed to implement the device in a microprocessor-based instrument.

SIGNAL RECEIVING AND STORAGE UNIT 20

The signal receiving and storage unit accepts and stores two types of information.

The first is an array of digital information transmitted from the pacemaker. This includes pacemaker programming information (the specific programmed values of all the pacemaker's programmable parameters), pacemaker stored patient related information (such as implant date, lead type and location, pre-implant symptoms, etc.), and results of automatically performed pacemaker measurements (such as lead impedance or battery level).

The second type of information is a predetermined length of N seconds (up to 30, 8 in preferred implementation) of synchronously sampled electrocardiographic signals, including atrial and ventricular intra-cardiac electrograms, a surface ECG signal, and pacemaker generated activity indicators (telemetered signals which identify specific actions taken by, or changes of state in, the implanted pacemaker, such as paced, sensed, end of refractory, etc.).

The atrial and ventricular intra-cardiac electrograms are sampled by the pacemaker, and digitally transmitted, along with the pacemaker activity indicators, to the device. The surface ECG signal is presented to the device as an analog signal. The devide samples this synchronously with the intra-cardiac electrogram sampling by taking a surface ECG sample at the time of receipt of every other intra-cardiac electrogram sample. The signal sampling sequence is: receive an atrial ICEG sample, receive a ventricular ICEG sample, take a surface ECG sample, receive an atrial ICEG sample, and so on.

The pacemaker activity indicators are transmitted by the pacemaker in lieu of ICEG samples, with a unique identifying code. Each activity indicator takes the place of one sample, so synchrony is maintained. (Note: The digital signal processing unit extracts each indicator from the ICEG data stream, and replaces the "missing" ICEG sample value with an interpolated value.

The pacemakeer stored information is received first, the the combined ICEG, ECG, and activity indicator signals. Processing of the information does not begin until all the signal information has been received and stored. The received ECG/ICEG signals are displayed on a real time analog display for the operator, and are continuously stored in a circular buffer holding N seconds of the digitized signals. When the operator is satisfied with the received signals, he indicates this, and the last N seconds (stored in the buffer) are saved for analysis.

DIGITAL SIGNAL PROCESSING UNIT 22

The purpose of the digital signal processing is to convert the continuous stream of digitized analog information into an ordered list of discrete events, and to characterize each event.

An event is defined as any interaction between the pacemaker and the heart, or any cardiac activity which should have caused a pacemaker response. These include (for either channel) spontaneous cardiac activity (whether sensed or not), pacemaker sensing of cardiac activity (whether of valid signal or of noise), pacemaker pacing outputs and cardiac evoked responses.

An event is characterized by a set of quantitative and symbolic metrics, including the time of occurrence, the channel on which it occurred, the presence or absence of spontaneous activity, whether or not the pacemaker sensed, and/or claimed (as shown by an activity indicator) it output a packing pulse, the presence or absence of a pacing pulse in the ECG signals, and the presence or absence of an evoked response. In addition, any other "special" information conveyed by the activity indicators (for example, an PVC indication) is included in the event description.

The presence of other pacemaker state changes which were signaled by an activity indicator (such as the end of a channel's refractory period) are identified, but not as separate events. Every event has appended to it a series of occurrence times, one for each possible pacemaker state change. If a particular state change happened between two events (after event A, but before event B) its time of occurrence in the description of the present event (event A) is set to a positive number, indicating how many milliseconds after the present event it occurred. A time of zero is used to indicate that no such change occurred between the present event and the next one.

The digital signal processing performs a six step process, as follows:
1. Signal sorting, activity indicator identification and removal,
2. ECG (including ICEG) signal verification,
3. Identification and removal of pacing spikes and atrifacts, 4. Detection of cardiac activity,
5. Correlation of cardiac activity and pacing spikes with activity indicators, and
6. Formatting the event list (for further analysis).

SIGNAL SORTING, ACTIVITY INDICATOR IDENTIFICATION AND REMOVAL

The sampled ICEG signals and the pacemaker activity indicators are received as a single multiplexed data stream. This is separated into three signals: the atrial ICEG, the ventricular ICEG, and the activity indicators. This is accomplished based on the known transmission sequence used by the pacemaker, and the unique codes which identify the activity indicators.

Next, since activity indicators are transmitted in place of ICEG signal samples, the ICEG signal timing will be corrected for any missing or time-shifted samples. In addition, since the atrial and ventricular ICEG samples are taken alternately, and the surface ECG samples are taken synchronously with every other transmitted sample (or inserted activity indicator), all sampled data and activity indicators must be corrected to produce a common sampling moment. These two steps are accomplished simultaneously. The result of this step is a set of four synchronously sampled signals; the surface ECG, the atrial and ventricular ICEGs, and the activity indicators. The received signals are sorted and corrected as indicated in the following Chart A:

"clean" enough for processing. The average and deviation of the signals are checked to determine if the overall signal level and the signal to noise level of each is acceptable, and each signal is checked for amplifier saturation following pacemaker output spikes.

If the signal is unsatisfactory, the user is informed (via the Results Output Unit) that the signal cannot be processed, and why. The device then stops and waits for the user to obtain another time segment of ECG/ICEG signals. FIGS. 4A–4E show examples of acceptable and unacceptable Atrial ICEG signals, with the surface ECG included for reference only. The signals shown are idealized versions for illustrative purposes; they are not real human data.

Identification and Removal of Pacing Spikes and Atrifacts

This step in the process locates and removes from each signal channel the pacing "spikes" and polarization artifacts caused by pacemaker outputs. This enhances the later identification of cardiac activity (either spontaneous or evoked).

Pacing spikes are identified in each channel by the presence of threshold crossings in the signal's derivative with a specified time relationship, based on the known pacemaker output pulse width. These spikes are then matched to pacemaker output activity indicators to determine on which channel the pacemaker output

CHART A
Signal Sorting, Activity Indicator Identification and Removal

A. ICEG and ECG Signals as Received
(Assuming 500 sample per second for each signal)

| Time (msec) | 1 | 2 | 3 | 4 | 5 | 6 | 7 | 8 | 9 | 10 | 11 | 12 |
|---|---|---|---|---|---|---|---|---|---|---|---|---|
| Telemetry | DA1 | DV1 | DA2 | DV2 | DA3 | DV3 | DA4 | PI1 | DA5 | DV5 | DA6 | DV6 |
| Surface ECG | | S1 | | S2 | | S3 | | S4 | | S5 | | S6 |

Where D and P are unique code indentifiers for ICEG data samples and pacemaker activity indicators, respectively; A1, V1, and S1 are sample number 1 of the Atrial ICEG, Ventricular ICEG, and Surface ECG signals, repectively; and I1 is the code for the pacemaker activity indicator number 1.

B. Stored Uncorrected Signal Data Files

| Time | A ICEG | V ICEG | S ECG | Act. Ind. |
|---|---|---|---|---|
| 1 | A1 | — | — | — |
| 2 | — | V1 | S1 | — |
| 3 | A2 | — | — | — |
| 4 | — | V2 | S2 | — |
| 5 | A3 | — | — | — |
| 6 | — | V3 | S3 | — |
| 7 | A4 | — | — | — |
| 8 | — | — | S4 | I1 |
| 9 | A5 | — | — | — |
| 10 | — | V5 | S5 | — |
| 11 | A6 | — | — | — |
| 12 | — | V6 | S6 | — |

C. Stored Corrected Signal Data Files
After Interpolation of V4, which was missing because of I1, and Correction of Atrial ICEG to Common Sampling Time)

| Time | A ICEG | V ICEG | S ECG | Act. Ind. |
|---|---|---|---|---|
| 2 | a1 | V1 | S1 | — |
| 4 | a2 | V2 | S2 | — |
| 6 | a3 | V3 | S3 | — |
| 8 | a4 | V4 | S4 | I1 |
| 10 | a5 | V5 | S5 | — |
| 12 | a6 | V6 | S6 | — |

Where a1 = (A1 + A2)/2 and V4 = (V3 + V5)/2

ECG Signal Verification

Before any further processing, the ECG and both ICEG signals are checked to determine if they are occurred. The time channel and occurrence for each pacing spike is stored, and all the pacing spikes are then removed, with a different method used for each channel.

The pacemaker spiked are removed from the surface channel by subtraction, and then the surface ECG signal is smoothed, by interpolation, to follow the "surrounding" evoked response.

Pacemaker spikes and polarization artifacts are removed from the channel on which the pacing spike occurred in a two step process. First, the pacing spike itself is subtracted. Next, the polarization atrifact is exponentially approximated using a second order linear predictor with a least squares estimator; this exponential is then subtracted. This allows the evoked response to be retained, even through it occurs in the middle of the exponential polarization atrifact.

Finally, pacing spikes due to pacemaker outputs on one channel are similarly removed from the other ICEG channel. In addition, the large "far field" polarization artifacts seen in the atrial channel due to ventricular outputs are exponentially removed.

The result of this sep is a set of ECG/ICEG signals with all pacing artifacts removed, but with all spontaneous and evoked cardiac activity retained. FIGS. 5A-5B illustrate this process. FIG. 5A shows a sampled ICEG (idealized) including a pacing spike and a repolarization atrifact. FIG. 5B shows the results of subtracting the pacing spike and the exponentially approximated repolarization atrifact. The remaining signal (shown as a sine wave) would represent the cardiac activity.

Detection Of Cardiac Activity

Cardiac activity (either spontaneous or evoked) is detected via a two-step process. First, a simple detector scans each signal channel for possible areas of activity. Next, a "smart" detector scans all three signals simultaneously, looking at each area identified by the simple detector.

The simple detector uses a level threshold to locate areas of possible cardiac activity. It independently scans each signal channel (surface ECG, atrial ICEG, and ventricular ICEG) to locate areas where the signal exceeds a defined threshold. The threshold is determined for each channel based on the mean, deviation, and peak values of the signal in that channel. The locations of these "candidate" areas are stored for use by the "smart" detector. (The primary purpose of this "simple" detector is to reduce the amount of signal the computationally intensive "smart" detector must process.)

The smart detector uses a set of "expectancy" matrices. These prestored matrices essentially contain what the device "expects" each type of event (atrial activity, ventricular activity, and noise) to look like across all three channels over a small sequence of samples. They were obtained by taking the mathematical inverse of "observed" signal matrices. The "observed" matrices were based on the combination of a large number of observations of each type of activity.

Figure 6:
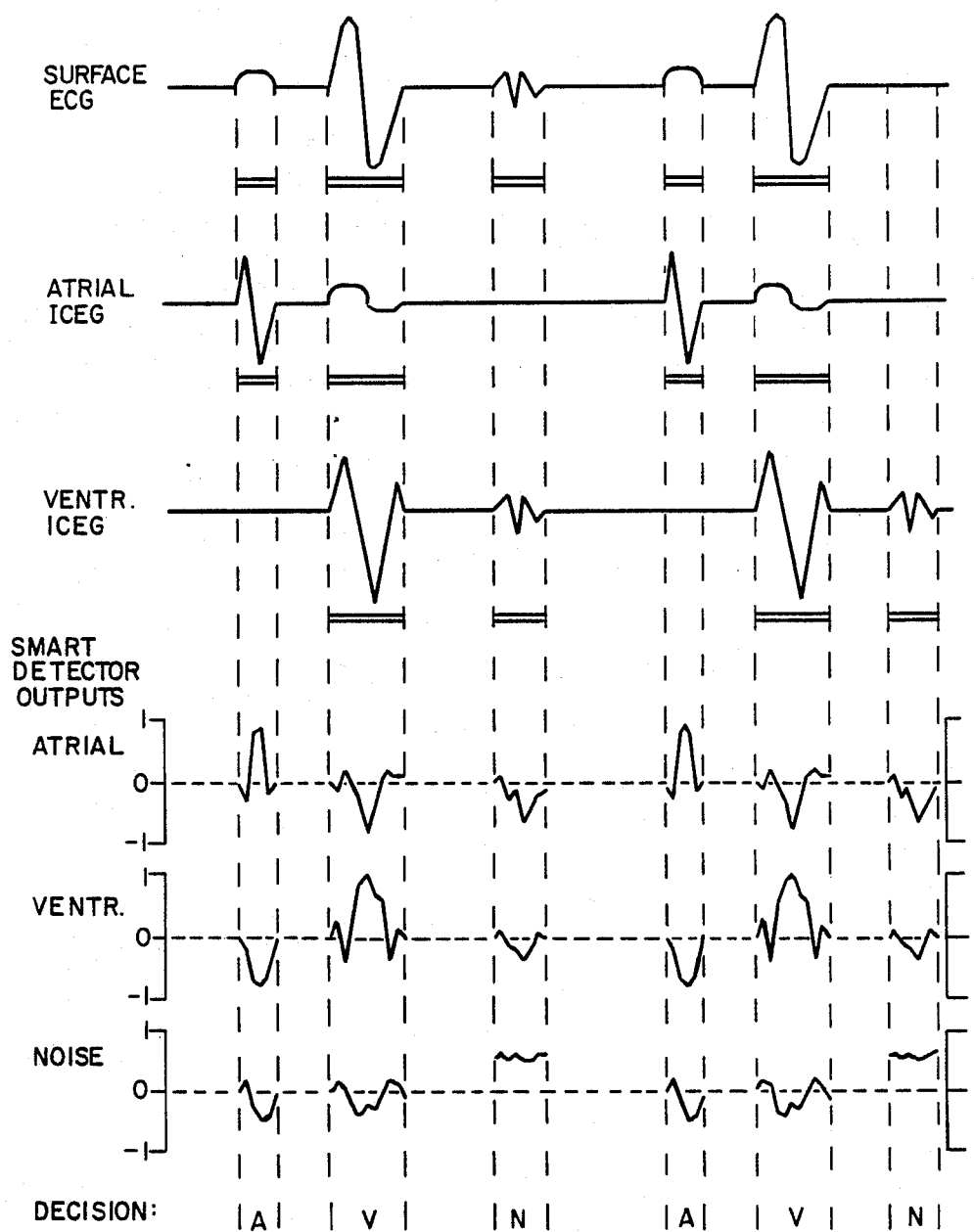
FIG. 6 illustrates the identification of cardiac activity.

The "smart" detector scans each type of expectancy matrix across all three simultaneous signals for each area identified by the "simple" detector, determining a "detector output" for each point in the candidate area. It also determines the first and second moment of the detector output. Based on these results, it selects the most probable identification of each candidate area (atrial activity, ventricular activity, or noise) and identifies the fiducial point (or common time reference point) for each area identified as cardiac activity. FIG. 6 illustrates this process. The upper section shows three (stylized) simultaneous data signals—the surface ECG, the atrial ICEG, and the ventricular ICEG. Immediately below each signal are indicated the "Candidate" areas identified by independently scanning each signal with the simple detector. The lower section shows the output of each of the smart detectors over each identified candidate area. These are obtained by independently scanning each smart detector over all three data signals simultaneously. Note that the outputs of the smart detectors exist only for simple detector identified candidate areas. The bottom line indicates the decision made about each candidate area, based on the relative outputs of the smart detectors. Each candidate area is identified as either atrial activity, ventricular activity, or noise (no cardiac activity).

Correlation With Activity Indicators

This step examines each identified occurrence of cardiac activity and attempts to associate it with a previously identified pacemaker action (such as a sense or a pace). For example, cardiac activity on a particular channel immediately following a pacemaker output on that channel would be considered as an evoked response, and would be evidence that the pacemaker output had "captured" the chamber. Those occurrences of cardiac activity which cannot be associated with an appropriate pacemaker activity indicator are retained as separate events. An example of this would be an unsensed P wave.

Formatting the Event List

The last step in the digital signal processing unit is to sequentially sort the identified events, and to write them in a standard format into the "event list". It is this list of discrete events that will be analyzed by the paced ECG event analysis unit. FIG. 7 shows the (stylized) surface ECG and the activity indicators for that section of the data. FIG. 8 is an event list corresponding to the data section of FIG. 7.

PACED ECG EVENT ANALYSIS UNIT 24

The purpose of the paced ECG event analysis unit is to examine each individual event and determine if the pacemaker functioned properly. For example, did it sense (or not sense) spontaneous cardiac activity when it was supposed to, did it output a pacing pulse at the correct time, did the pacing pulse capture the heart (produce an evoked response in the paced chamber), did the refractory periods end on time, were there any occurrences of PVCs, PACs, or special pacemaker mediated events, etc.

As each event is analyzed, several status indicators are determined for each event. These include sensing status, pacing (timing) status, capture status, state change timing (such as end of refractory period) status, and special (PVC, anti-PMT dropped beat, ventricular safety pace beat, etc.) statuses. The possible values for each status indicator include all possible normal and abnormal functional conditions for that pacemaker function. For example, the possible values for sensing status include three normal conditions (OK) and five abnormal conditions (NG), as follows:

| STATUS | MEANING |
|---|---|
| OK - Unobserved: | No cardiac activity and no sense indicator, |
| OK - Ignored: | Cardiac activity properly not |

| STATUS | MEANING |
| --- | --- |
| | sensed, |
| OK - Sensed: | Cardiac activity properly sensed, |
| NG - Undersense: | Cardiac activity not sensed when it should have been, |
| NG - Oversense: | Sense indicator with no cardiac activity, |
| NG - Sense in Off: | A sense indicator from a channel with sensing turned off, |
| NG - Sense in Blanking: | A sense indicator during the blanking period of a channel, |
| NG - Indicated Sense In Noise Window | Sense indicator during special noise blanking period. |

Since is is possible for several abnormal conditions to occur at the same time (for example, an oversense in the blanking period), the unit identifies the most serious problem, and assigns that status indicator value for the event.

The paced ECG event analysis unit is based on a detailed model of the functioning relationships incorporated in the pacemaker's hardware and software, expressed as a set of logical rules. These rules predict exactly what the pacemaker is expected to do in any situation, based on the programmed parameter values. The unit compares the expected functioning (as predicted by the model) with the observed functioning (as evidenced by the event list) to determine the status of each pacemaker function for each event.

Figure 9:
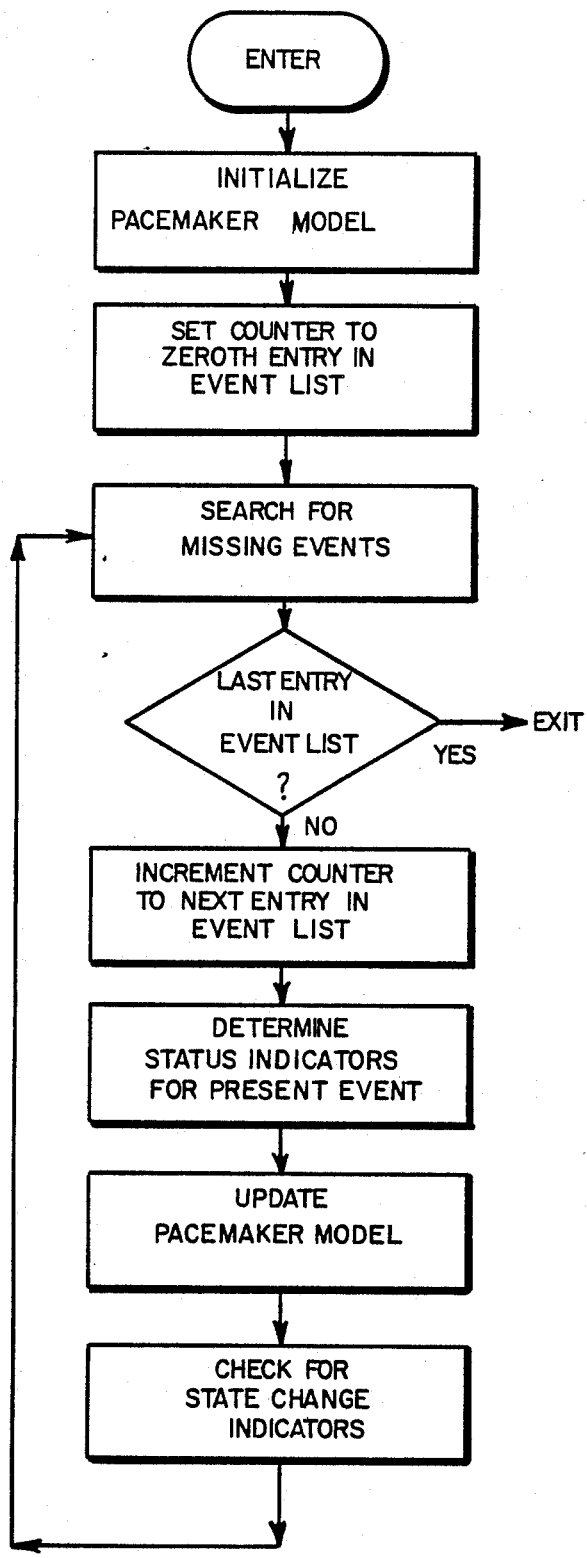
FIG. 9 is an overall flow chart for the paced ECG event analysis unit.

The paced ECG event analysis unit performs a five step process, with the last four steps repeated sequentially for each entry in the event list, as follows:
1. Initialization,
2. "Missing" event detection,
3. Status indicator determination,
4. Update the model, and
5. Check for ("non-event") state change indicators.
FIG. 9 shows the overall flow of information in this unit.

Initialization

In order to determine how the pacemaker should act at a given moment it is necessary to know the "state" of the pacemaker; i.e., the value of every variable in the pacemaker at that moment in time. For example, to determine if the pacemaker should sense a P-wave, it is necessary to know if atrial sensing is on or off, and, if it is on, is the channel blanked, refractory, alert, or in a noise window. The values of these internal pacemaker variables depend on both the programmed parameter values and the past experience (history) of the pacemaker. While all programmed parameter values are known, the history of the pacemaker is not known at the beginning of the ECG/ICEG data segment. Initialization establishes its state.

Figure 10:
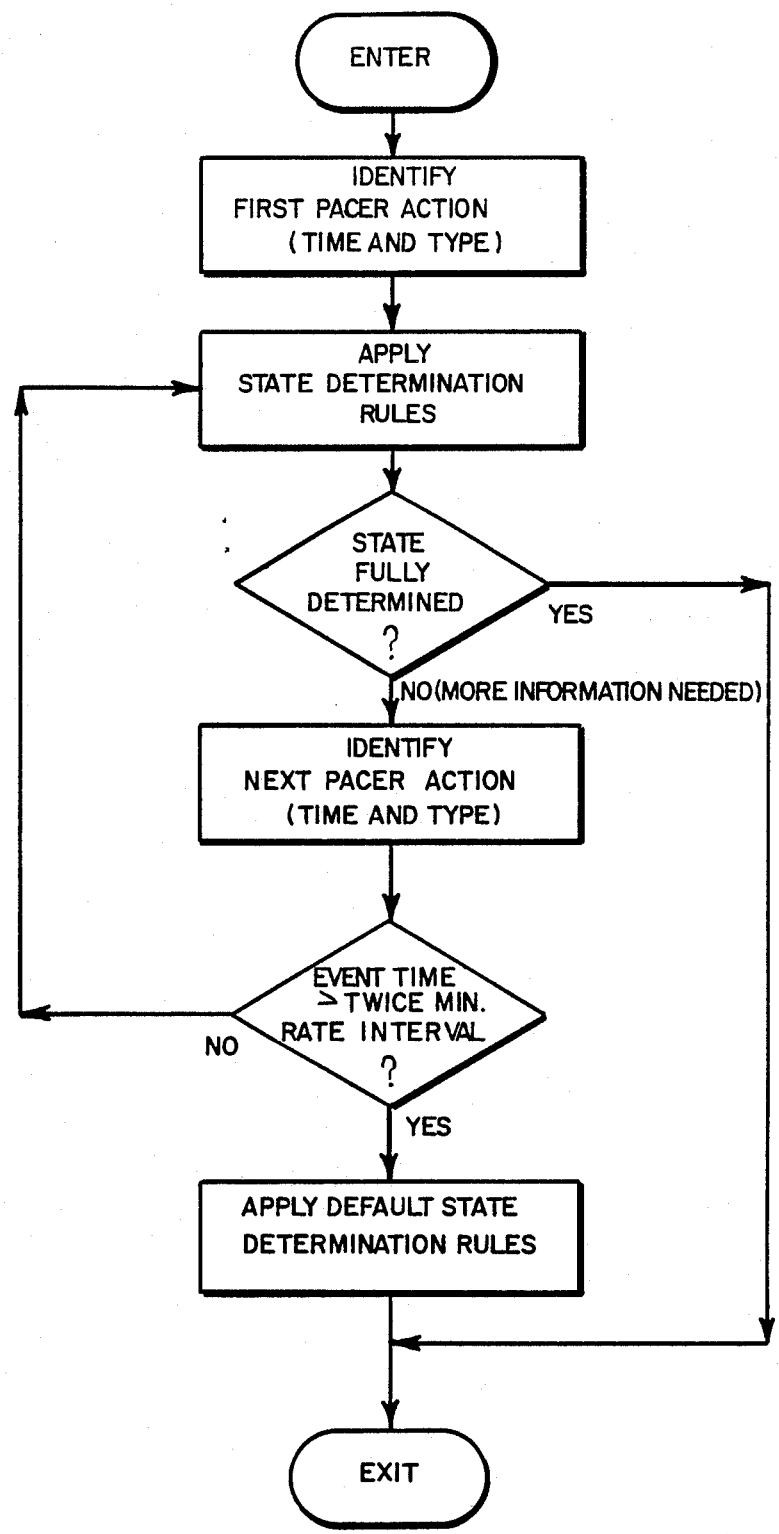
FIG. 10 is a flow chart showing the initialization step of the paced ECG analysis.

Initialization is accomplished by assuming that the pacemaker is functioning properly, and examining how it acted in response to the heart's actions early on in the data segment. For example, if a DDD pacemaker's first action was to pace the atrium, then it is assumed to have been in the atrial escape interval at the start of the data segment. Since both the number of possible pacemaker states and the number of first actions are finite (though large), an exhaustive analysis of the responses to initial actions allows the pacemaker's state at the start of the data to be uniquely determined. Once the initial state of the pacemaker has been determined, each subsequent event can then be sequentially analyzed. FIG. 10 shows the sequence of information flow for this unit.

Missing Event Detection

Figure 11:
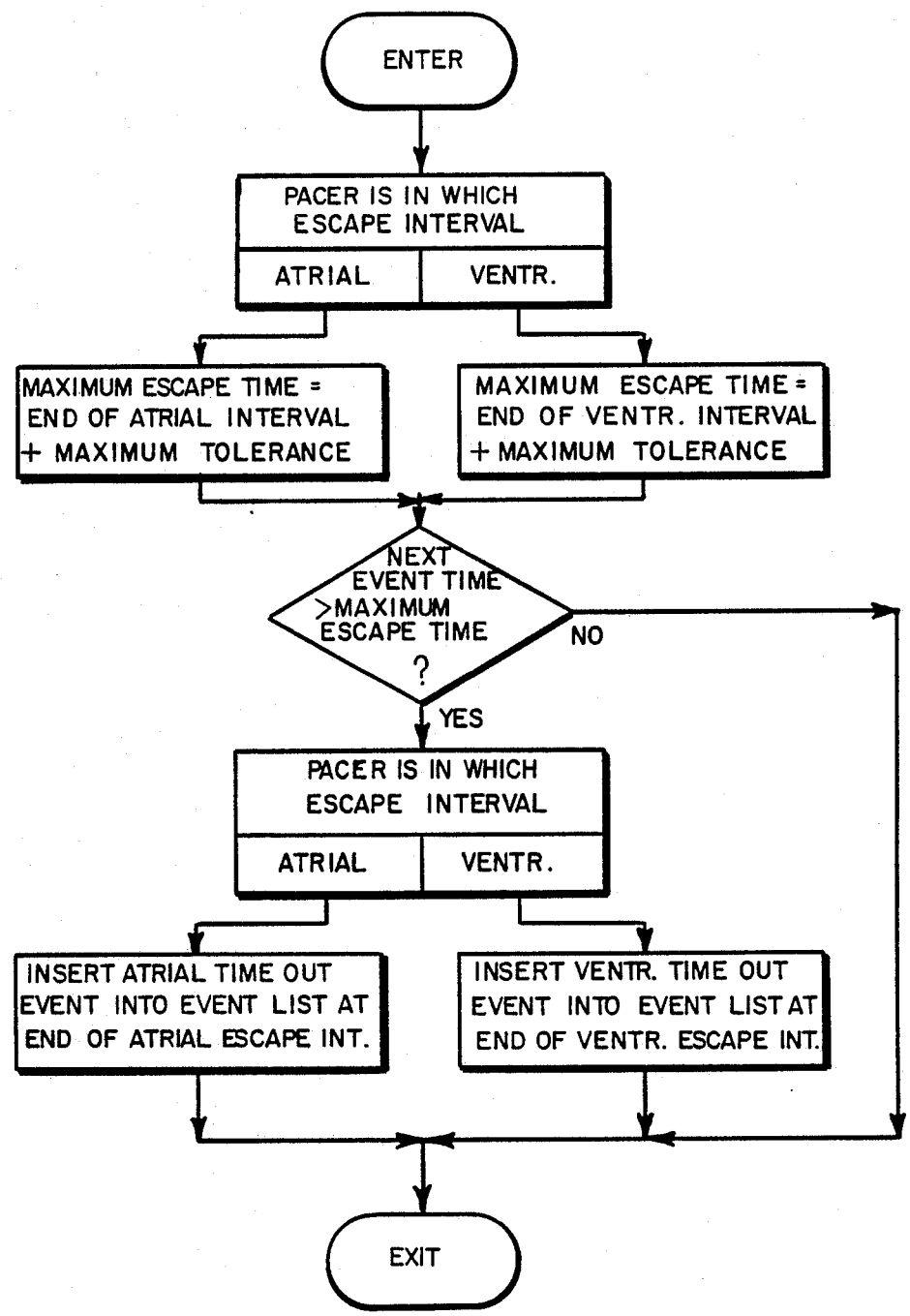
FIG. 11 is a flow chart showing the missing event determination step of the paced ECG event analysis.

The analysis of each event begins by checking to see if any event should have occurred after the last analyzed event and prior to the specific event that is about to be analyzed; i.e., is any expected event "missing." This can occur for two reasons, pacemaker malfunction or unobserved pacemaker state changes. If a "missing event" is identified, it is inserted into the event list ahead of the event about to be analyzed. The inserted "missing" event will be analyzed next, before the event that was about to be analyzed. Examples of each type of "missing event" follow. FIG. 11 shows the decision structure for identifying "missing" events.

Suppose that a VOO pacemaker is programmed to 60 beats per minute, and that the interval from the previous event (a ventricular pace) to the event about to be analyzed in the event list is 1,200 milliseconds. Obviously, the pacemaker should have output a pulse 1,000 milliseconds after the previous event, and did not—it malfunctioned. This is accommodated by adding an event to the event list at 1,000 milliseconds after the previous event (200 milliseconds before the event that was about to be analyzed). When this "added" event is analyzed, it will indicate a failure to pace when expected.

However, "missing events" can also occur during normal pacemaker functioning. For example, consider a VDD pacemaker. Assume that following a ventricular pace, no atrial activity is detected for the entire minimum rate determined beat to beat interval. The pacemaker would then correctly pace the ventricle. However, the atrial escape interval has ended and the ventricular escape interval (or AV delay) has started with no activity indicator. To allow the model to correctly process this state change, an event would be added to the event list at the expected end of the atrial escape interval. (This is identified as a "phantom" event and is only used internally for analysis; it is not identified as an event to the user.)

Status Indicator Determination

Knowing the state of the pacemaker, it is possible to determine if it functional properly at each event. Each event is analyzed, based on the metrics determined by the digital signal processing unit. A single value is assigned to each status for every event.

Separate rules evaluate the various functions and determine the value of each status indicator for the event. A typical rule from the evaluation of capture status might read:

| IF | Pacing output is present and evoked response is present |
| --- | --- |
| THEN | Capture status is "OK - captured" |

The rules used are based on a rigorous, exhaustive analysis of all possible combinations of relevant event metrics and pacemaker programmed parameter values, and were verified by clinical experts. The rules are independent of the channel where the event occurred, except for events such as premature ventricular contractions or retrograde P waves, which can occur only on a specific channel.

Update the Model

Each event may change the state of the pacemaker. This will affect the way in which it responds to the next event. This step in the paced ECG event analysis determines the way in which the state of the pacemaker has been changed by the event just analyzed. In essence, it "updates" the running model of the pacemaker, and prepares it to evaluate the next event. The following Chart B shows the input variables used by, and the possible outcomes for, each set of event status determination rules—sensing, pacing (timing) and capture. Note that the same rules apply to both the atrial and ventricular channels, and are applied independently to each.

CHART B
Status Indicator Determination

A. Sensing Status
Input Variables
Sense Amplifier State: Off, Blanked, Refractory, Alert, Noise Window/Possible, Noise Window/Definite
Spontaneous Cardiac Activity: Absent, Present
Sense Activity Indicator: Present, Absent
Possible Outcomes
OK - Unobserved
OK - Ignored
OK - Sensed
NG - Undersense
NG - Oversense
NG - Sense When Off
NG - Sense in Blanking
NG - Sense in Noise Window B. Pacing (Timing) Status
Input Variables
Mode
Pacing: Off, On
Sensing: Off, On
Triggering: Off, On
Event Time = End of Escape Interval (within allowed Minimum and Maximum Tolerance): No, Yes, Uncertain
Correct Sense (Sense when not Refractory and not in Ventricular Safety Pace Window): No, Yes
Pace Activity Indicator: Absent, Present
Possible Outcomes
OK - No Output Expected
OK - No Output Expected/Phantom
OK - Output When Expected
OK - Output Timing Uncertain
NG - No Output When Expected
NG - Output When Not Expected
NG - Output Triggering
NG - Output When Off C. Capturing Status
Input Variables
Pace Activity Indicator: Absent, Present
Pacing Output Pulse: Absent, Present
Spontaneous Cardiac Activity: Absent, Present
Evoked Response: Absent, Present
Possible Outcomes
OK - Unobserved, No Pacer Output
OK - Unobserved, Competitive Pacing
OK - Captured
NG - No Capture Observed
NG - No Capture, Output Pulse Missing It is based on the detailed model of the pacemaker functional relationships and the programmed parameter values. However, the model has been expended to allow for uncertainties due to both real world timing tolerances and imprecise or incomplete history.

Figure 12:
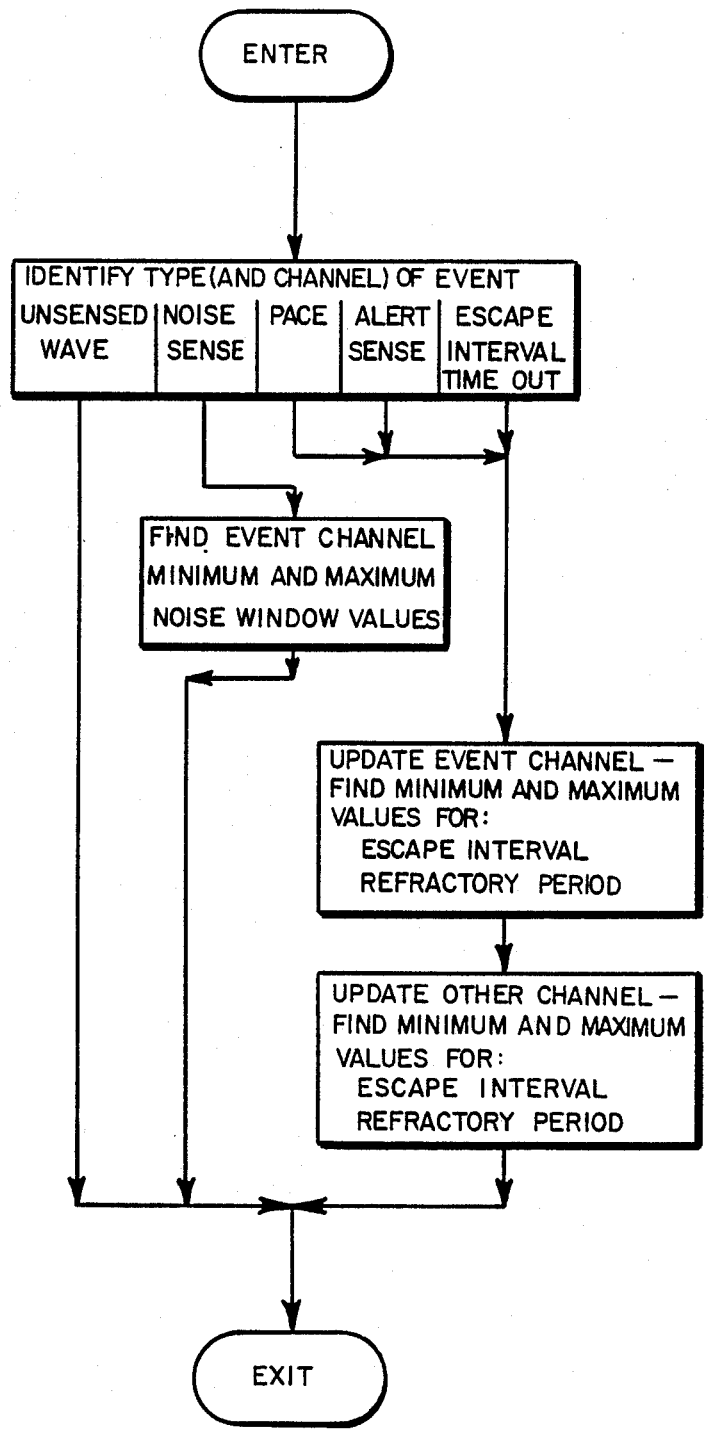
FIG. 12 is a flow chart showing the updating step of the paced ECG event analysis.

For example, the duration of the AV delay may be a function of whether or not the two previous atrial events were paced or sensed. If this is not shown (such as on the second beat), the model would be updated to show a range of allowable AV delays, based on however much history is known. When the next ventricular event is analyzed, AV delays falling anywhere in this range would be considered correct functioning. FIG. 12 shows the steps involved in updating the pacemaker model, depending on the type of event that has occurred. Note that the process is similar, regardless of the channel on which the event occurred.

Check For State Change Indicators

Certain state changes within the pacemaker are signaled by telemetered activity indicators, but are not considered as pacemaker/patient events. They were indicated in the event list by noting the time they occurred after the immediately preceding true event. The last step in the analysis of a single event is to look for any such indicators and verify their function and timing. The following Chart C shows the input variables and possible outcomes for a typical state change activity indicator status determination, the end of refractory period activity indicator. Note that the same rules apply to both the atrial and ventricular channels, and are applied independently to each.

CHART C
State Change Indicator Status
End of Refractory (EOR) Activity Indicator Status Input Variables
Channel Refractory: No, Yes
EOR Minimum Time After This Event, Before Next Event: No, Yes
EOR Nominal Time After This Event, Before Next Event: No, Yes
EOR Maximum Time After This Event, Before Next Event: No, Yes
EOR Activity Indicator: Absent, Present
EOR Activity Indicator Time: Less Than EOR Minimum Time, Between Minimum and Maximum. Greater Than EOR MAximum Time
Possible Outcome
OK - No EOR Activity Indicator Expected
OK - EOR Activity Indicator On Time
NG - EOR Activity Indicator Early
NG - EOR Activity Indiator Late
NG - EOR Activity Indicator Missing
NG - Extra EOR Activity Indicator This completes the analysis of an event in the event list. The last four steps are repeated until the end of the event list is reached.

CLINICAL ANALYSIS AND ADVISOR UNIT 26

The purpose of the clinical analysis and advisor unit is to combine the results of the analyses of the individual events into a single comprehensive evaluation of the implanted cardiac pacemaker system.

Following the paced ECG event analysis, the event list contains the signal analysis metrics and statuses for each patient/pacemaker interaction or event. The clinical analysis and advisor unit uses expert system techniques to combine the information in the event list with patient and pacemaker data, and a knowledge base of clinical expertise in ECG problem solving to produce a summary analysis of the functional condition of the implanted pacemaker; including any identified problem(s), their probable cause(s), and clinically acceptable actions to correct them.

The clinical analysis and advisor unit uses a clinical knowledge base organized into a series of frame-like structures; that is, separate structures for problems relating to pacing leads, pacing rate, pacemaker electronic malfunctions, pacing and sensing thresholds, pacing lead configurations, etc. This allows the unit to search the knowledge base much as a clinician would analyze a paced ECG in actual practice.

This structuring also allows each step of the analysis to be individually examined and validated. Because each structure covers a limited and defined domain (set of possible inputs, problems, and causes) it can be rigorously validated, often by exhaustive search of all possible input combinations and their resulting outputs. This is typically not possible in most expert systems which do not employ such a frame-like structuring.

The clinical analysis and advisor unit uses a four step process, as follows:

1. Data reduction (and summarization),
2. Problem identification,
3. Determination of problem causes, and
4. Provision of clinical advice.

Figure 13:
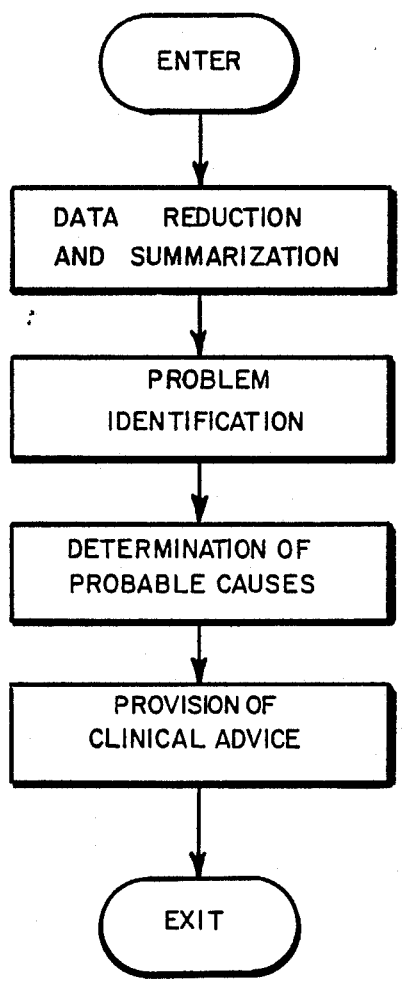
FIG. 13 is a flow chart showing the clinical analysis and advisor unit.

FIG. 13 shows the sequence of events in this unit.

In the present implementation, steps three and four of this process were combined into a single step. Therefore, in the following descriptions, the purposes of these last two steps will be separately described, and then their implementation as a single step will be described.

Data Reduction

To allow the clinical analysis and advisor unit to examine and sort out the large amount of information presented to it in any reasonable time, data reduction is necessary. This is accomplished in four separate areas; reduction of programmed parameter and stored patient information values, reduction of strings of events into the larger clinical P-QRS complexes called "beats," identification of clinically significant ECG patterns over multiple events, and summarizing of common event status values. These reductions are accomplished by the sequential application of a series of pre-stored rules or "Productions" in an "IF (FACTS) . . . THEN (ACTIONS) . . . " format, and random access memory search and update methods.

The number of programmable parameter values stored in the pacemaker can cause a combinatorial explosion, results in an unmanageable number of logic tests being needed to arrive at a single analysis result. These programmable parameter values are reduced to a manageable number by symbolic representations. For example, a pacemaker may have up to 128 possible combinations for pacemaker output amplitude and pulse width. This is first reduced by combining the two values into a single value representing the total charge delivered by the output. This might reduce the 128 values by more than half. Next these charge values are ordered and identified as falling into one of five clinically significant symbolically labelled categories. A set of 40 charge values might be labelled as follows:

Minimum - Lowest (Value 1)
Low - Next 9 (Values 2 through 10)
Mid Range - Next 20 (Values 11 through 30)
High - Next 9 (Values 31 through 39)
Maximum - Highest (Value 40)

A similar example is the reduction of the stored implant date and the present date into a single designation of whether the implant is "acute" or "chronic."

The second data reduction is performed primarily to reduce the amount of information that will have to be presented to the clinician. Separate events are combined into larger P-QRS complexes identified as "beats." This allows the conversion of references from the exact time domain into the clinical terms normally used in discussing ECGs. Thus, rather than reporting an atrial event which occurred at 2895 milliseconds into the data segment, the device can refer to the atrial part of P-QRS beat 3. This reduction is accomplished by a set of rules that examine the order and type of atrial and ventricular events within specific time limits.

Productions are also used to combine the order and timing of individual events to identify ECG occurrences that happen over several beats, such as retrograde P waves, premature ventricular contractions, or pacemaker mediated tachycardia. These identifications are added to the individual event descriptions in the Event List before summarization.

At the same time, questionable occurrences are examined and verified. For example, it is not always possible to directly verify atrial capture, since the atrial evoked response is not always clearly identifiable in the ECG or ICEG. Digital signal processing may fail to identify it, with the result theat atrial capture status is classified as "unknown." However, by examining a series of events, there may be "further evidence" indicating atrial capture. If there are instances where atrial paced events are consistently followed by spontaneous ventricular contractions within a normal AV delay range, then atrial capture can be assumed to have occurred, and the atrial capture status is changed to "OK—Captured."

Figure 14:
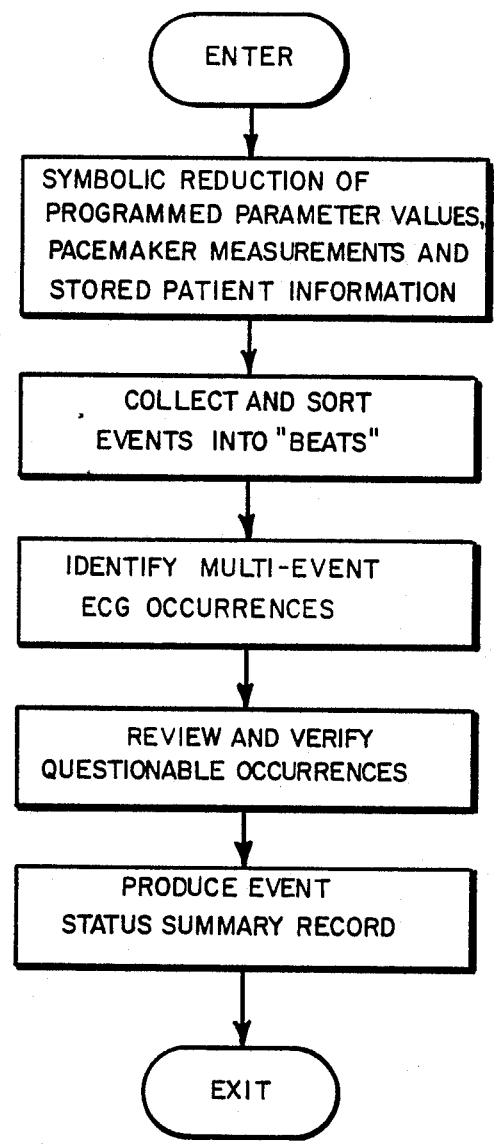
FIG. 14 is a flow chart showing the data reduction and summarization step of the clinical analysis and adviser unit.

Finally, the entire list of individual events and their separate status values are summarized to produce a single event status summary record. This summary contains, for each channel, the type of event (sensed, paced, etc.) and the common status values found in the different beats. It is this event status summary record, in combination with pacemaker and patient data, which is primarily used for problem identification. FIG. 14 shows the sequential flow of these activities. FIG. 15 shows the event status summary record that would be produced for the sample (stylized) surface ECG shown in FIG. 15B. The record is based on the analysis of all the signals, not just the surface ECG. The surface ECG is included here for illustrative purposes only.

Problem Identification

Once the event status summary record has been produced, it is scanned via a computed "key" access (based on the channel, the number of records, and status indicator) to the record, to determine the operational status of each of the pacemaker's functions (sensing, pacing, timing and capture) for each channel. The productions examine the status indicator values for each particular function for all events. Functions are identified as having one of four operational states, as follows:

Unobserved: The particular function was never observable during the ECG data segment. (Example: Atrial sensing when no P waves were present.)

Normal: The particular function was observable at least once during the ECG data segment; and its status was OK every time it was observed. (Example: Proper atrial sensing of intermittent P waves with no over-sensing when P waves not present.)

Abnormal-Intermittent: The particular function was observable at least twice during the ECG data segment; its status was OK at least once and No Good at least once. (Example: Multiple paced atrial beats, with the atrium captured on some beats and not on others.)

Abnormal—Complete (or Constant): The particular function was observable at least once during the ECG data segment; its status was No Good every time it was observed. (Example: One or more paced atrial beats, none of which captured the atrium.)

In addition, any special status indicators are reviewed for possible improper functioning.

Where any abnormal functioning is identified, the beats on which the function's status was No Good are noted. These will be reported to the clinician.

At this stage in its analysis, the device has simply "reviewed" the ECG and "reported" its findings, "flagging" any abnormalities. There has been no identification of the possible causes of any of the observed abnormalities, and no determination of future clinical actions, either diagnostic or therapeutic. In certain applications, this would be the appropriate termination of the analysis. In those cases, the remaining stages in the clinical analysis and advisor unit would be disabled, and the present coded analysis results would be directly passed to the results output unit.

Figure 16:
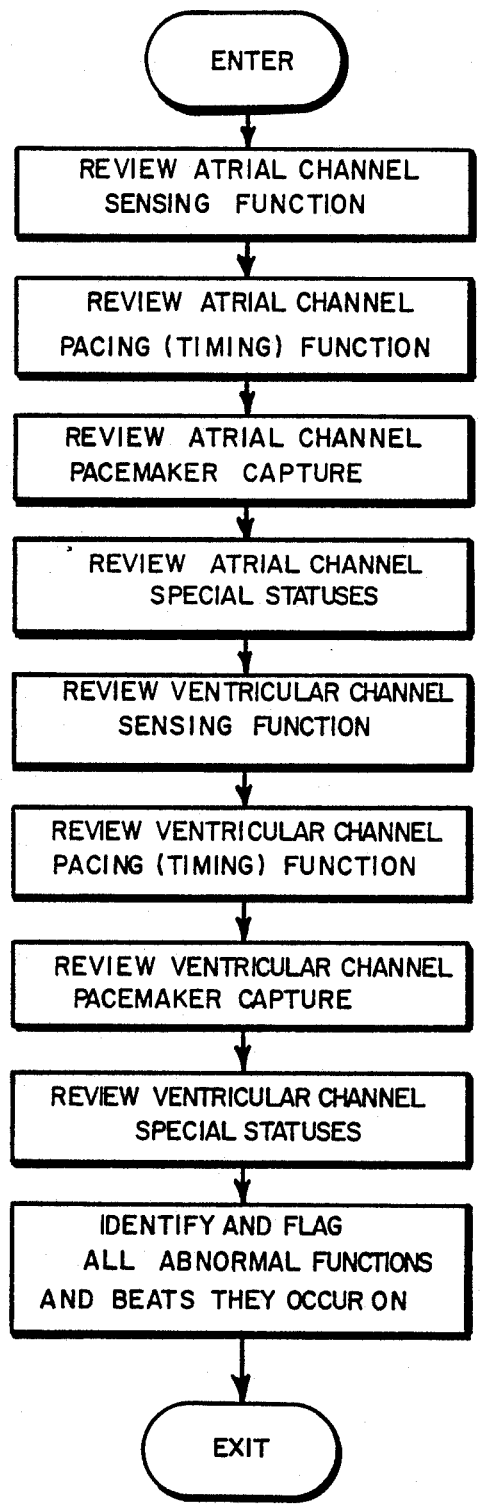
FIG. 16 is a flow chart showing the problem identification step for the clinical analysis and advisor unit.

FIG. 16 shows the sequential identification of problems with each of the different pacer functions.

Determination of Problem Causes

Once individual problems (or malfunctions) have been identified, the device must determine what caused the problem(s). Because of the complex interactions within the implanted system, multiple observed problems may in fact have a common cause. For example, a dislodged atrial lead could cause both intermittent atrial under sensing and complete loss of atrial capture; in the presence of retrograde conduction, this could also yield retrograde P waves. Alternately, consistent atrial undersensing along with complete loss of atrial capture could be due to an atrial lead problem (fracture, dislocation, etc.) or to separately programmed inappropriate values for atrial output and atrial sensitivity.

Problem causes are grouped by engineering system (pacemaker timing control, output circuits, sensing circuits, leads, etc.), with each system being sequentially examined. The stored knowledge base used to identify problem causes is based upon a structured representation of information derived primarily from pacemaker system engineers, and secondarily from experienced clinicians, obtained through both reviews of published material and extensive interviews.

Because specific system malfunctions may cause multiple observed problems, it is necessary to examine not only separate observed problems, but also combinations of problems. To assist in identifying problem causes, stored information (such as pacemaker measurements and stored patient information) as well as programmed parameter values are combined with the information on the observed problems. Where a single cause cannot be positively identified, multiple possible causes are retained.

Provision Of Clinical Advice

Once the causes of the observed pacemaker system problems have been identified, possible corrective actions can be identified. Determining the proper action to correct a specific problem is a clinical task, clearly requiring an experienced medical practitioner. The device's ability to recommend actions is severely constrained by both ethical and legal considerations. It is not within the scope of any device to practice clinical medicine. However, it is within the scope of this device to provide the clinician with a set of reminders, encompassing clinically accepted techniques for rectifying each identified problem, along with a list of "relevant" patient and/or pacemaker information.

Another knowledge base (obtained primarily from clinical experts) is used to identify appropriate and generally accepted clinical procedures. These may include both specific actions (such as reprogramming the pacemaker) and diagnostic procedures (such as fluoroscopic examination of the lead). The recommendations are based not only on the observed problem, but also on stored information about the pacemaker and the patient. For example, increasing the pacemaker's output would not be recommended if the pacemaker were already at maximum output, while reducing the pacing rate to attempt to observe atrial sensing would not be recommended if the patient has a pre-pacing history of syncope.

In addition to identifying possible actions, the device also identifies specific facts from the stored information which are relevant to the actions identified. These are passed to the results output unit along with the actions.

Joint Implementation—Determination Of Problem Causes and Provision Of Clinical Advice In its present implementation, the two separate steps of determination of problem causes the provision of clinical advice have been combined into a single step. The two separate knowledge bases were combined into a common sets of productions with a single inference engine.

As in other units, the productions in this step use the "IF (FACTS) . . . THEN (ACTIONS) . . . " structure. FACTS are the combinations of symbolic representations of the stored pacemaker data, quantitative and symbolic paced ECG event metrics, and the summary of the statuses for each event. Each "FACTS" part of a production essentially represents a possible problem state. The "ACTION" part of a production contains relevant pacemaker programmed variables to be displayed, a statement of both normal and abnormal events and where they occur (P-QRS beats), the probable cause of the abnormal event, some reasoning about the event (if possible) and recommendations for actions to correct the problem.

An example of a production from this step is:

| | |
|---|---|
| IF | COMPLETE LOSS of (channel) SENSING and (channel) SENSITIVITY is MAXIMUM and COMPLETE LOSS of (channel) CAPTURE and (channel) OUTPUT is HIGH and (channel) IMPLANT-TIME is ACUTE |
| THEN | Display: (channel) SENSITIVITY value |
| | Display: (channel) OUTPUT value |
| | Display: "Examine (channel) lead for possible repositioning." |
| | Display: "Watch for Diaphragmatic Stimulation due to the HIGH OUTPUT value." |

The productions are grouped (framed) into problem categories. That is: pacemaker malfunctioning, pacing leads, pacing and sensing thresholds, pacing rate, etc.

Figure 17:
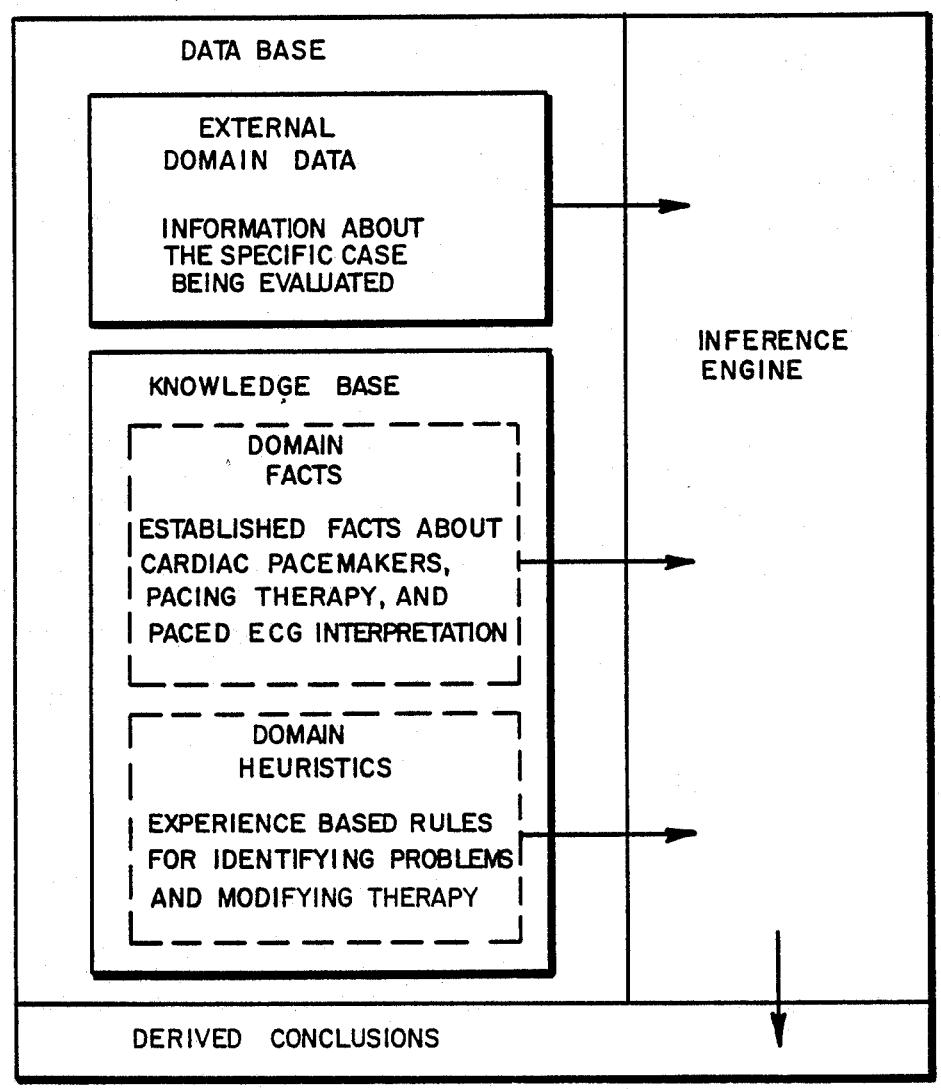
FIG. 17 is a flow chart showing the step of determining problem causes and providing clinical advice by the clinical analysis and advisor unit.

The mechanism to search through the entire knowledge base of productions is called an "inference engine." Each production is examined, and if the "FACTS" part is true, then the production is instantiated and the "ACTIONS" occur. If false, then the search continues to process the other productions. The order of the search through the productions emulates the way in which a clinician would view and analyze a patient's paced ECG. FIG. 17 shows the structure of the Expert System that is used for the joint implementation of these two steps, indicating the types of information stored in each section of the data base.

RESULTS OUTPUT UNIT 28

The purpose of the results output unit is to present the conclusions from the analyses to the clinician. Depending on the capabilities of the output unit, results may be presented either as a single entity or as a sequential series of presentations, either on a visual display or in "hard copy."

Regardless of the output mechanism used, the results output unit performs several functions. First, it combines the stored surface ECG with the derived beat identifications and stored activity indicators to provide an annotated ECG. Second, it provides a display of the summarized results for each channel, identifying all observed and unobserved functional status for each channel, with all abnormal findings clearly labelled. Finally, for every abnormal finding, it lists the relevant pacemaker and patient data, the probable causes, and possible corrective actions.

This unit includes large scale editing and code conversion sections, to convert the internal coded information into specific user readable outputs, tailored to the specific display being used, as well as the connectors and drivers for the actual output unit employed.

Although an illustrative embodiment of the invention has been shown and described, it is to be understood that various modifications and substitutions may be made by those skilled in the art without departing from the novel spirit and scope of the present invention.

What is claimed is:

1. A cardiac pacer analysis system, which comprises:
   means for receiving and storing information telemetrically transmitted from an implanted pacer;
   means for identifying and characterizing events in the received information;
   means for identifying observed problems that are based on the events and on logical rules which express the functioning relationships incorporated in the operation of the implanted pacer;
   means for automatically determining probable causes of observed problems and possible corrective actions; and
   means for displaying the results of the automatic determinations to a clinician by including selected clinically relevant information.

2. A system as described in claim 1, in which the information received includes pacer parameter programmed values, pacer stored patient-related information, results of automatically performed pacer measurements, and a surface ECG signal presented as an analog signal.

3. A cardiac pacer analysis system as described in claim 1, including means for automatically providing a sampling segment, checking the sampling segment to determine if it is satisfactory for reference purpose, identifying proper pacing spikes and removing the improper spikes, detecting the cardiac activity, and correlating the detected cardiac activity with previously received information.

4. A cardiac pacer analysis system as described in claim 1, including means for automatically comparing observed events with model information that is previously stored in the analysis system, including means for automatically determining the initial state of the pacer, checking for missing events, determining if the pacer is functioning properly at each of the observed events, updating the stored model information to prepare for evaluating the next event, checking for state changes within the pacer, and providing an event list based on said comparison.

5. A cardiac pacer analysis system as described in claim 4, including means for automatically reducing the amount of received data, summarizing the events to produce a summary record, identifying the operational status of each of the pacer's functions for each channel, noting any abnormal function, comparing abnormal functioning data with previously stored information to determine problem causes, and displaying recommended corrective action.

6. A cardiac pacer analysis system which comprises:
   a signal receiving and storage means for accepting surface ECG and telemetrically transmitted information from the pacer and storing said information;
   a digital signal processing means responsive for the signal receiving and storing means for identifying and characterizing the received ECG data;
   an ECG event analysis means responsive to the digital signal processing means for automatically determining if the pacer functioned correctly and produced the clinically desired response from the patient at each ECG event;
   a clinical analysis and advisor means responsive to the ECG event analysis means for automatically summarizing the results and identifying any observed problems and automatically providing probable causes and possible actions that a physician can take to alleviate the observed problem; and
   a results output means for automatically presenting results of the ECG event analysis and the clinical event analysis by including selected relevant clinical information to a clinician.

7. A cardiac pacer analysis system for use with a cardiac pacer in which patient history information is stored within the pacer, which comprises:
   storage means containing a knowledge base encompassing the functional characteristics of the pacer;
   means for automatically receiving information including surface ECG information and telemetered ICEGs from the pacer;
   means for automatically sorting by time and type of signal the received information signals and providing a sampling segment;
   means for automatically examining each sampling segment to determine if the pacer functions properly; and
   means for automatically analyzing the received information to provide a comprehensive assessment of the implanted pacer.

8. A system as described in claiim 7, in which the information received includes pacer parameter programmed values, pacer stored patient-related information, results of automatically performed pacer measurements, and a surface ECG signal presented as an analog signal.

9. A cardiac pacer analysis system as described in claim 7, including means for automatically checking the sampling segment to determine if it is satisfactory for reference purpose, detecting the cardiac activity, and correlating the detected cardiac activity with previously received information.

10. A cardiac pacer analysis system as described in claim 7, including means for automatically comparing observed events with previously stored model information, including means for automatically determining the initial state of the pacer, checking for missing events, determining if the pacer is functioning properly at each of the observed events, updating the stored model information to prepare for evaluating the next event, checking for state changes within the pacer, and providing an event list based on said comparison.

11. A cardiac pacer analysis system as described in claim 10, including means for reducing the amount of received data, summarizing the events to produce a summary record, identifying the operational status of each of the pacer's functions for each channel, noting any abnormal function, comparing abnormal functioning data with previously stored information to determine problem causes, and displaying recommended corrective action.

12. A cardiac pacer analysis system as described in claim 7, in which the pacer stored patient-related information includes the implant date, lead type and location, and pre-implant symptoms.

13. A cardiac pacer analysis system as described in claim 7, in which the pacer's functions include sensing pacing timing and capture for each channel.

14. A cardiac pacer analysis system which comprises:
means for receiving and storing telemetrically transmitted information, including pacer parameter programmed values, pacer stored patient-related information, results of automatically performed pacer measurements, and a surface ECG signal presented as an analog signal;
means for automatically sorting the signals and producing a sampling segment;
means for automatically detecting cardiac activity and correlating the detected cardiac activity with a previously identified pacer action;
means for automatically sorting the identified events;
means for automatically examining each event and determining if the pacer functions properly; and
means for automatically providing a comprehensive evaluation of the implanted pacer.

15. A cardiac pacer analysis system as described in claim 14, in which the providing means includes means for automatically reducing the amount of received data, summarizing the events to produce a summary record, identifying the operational status of each of the pacer's functions for each channel, noting any abnormal functioning, comparing abnormal functioning data with previously stored information to determine problem causes, and displaying recommended corrective action.

16. A cardiac pacer analysis system as described in claim 14, including means for automatically comparing observed events with previously stored model information, said comparing means including means for automatically determining the initial state of the pacer, checking for missing events, determining if the pacer is functioning properly at the observed event, updating the stored model information to prepare for evaluating the next event, and checking for state changes within the pacer.

* * * * *